United States Patent [19]

Strassmann

[11] Patent Number: 5,087,453
[45] Date of Patent: Feb. 11, 1992

[54] METHOD FOR THE TREATMENT OF BACTERIAL CAUSED WEIGHT LOSS AND/OR HYPOGLYCEMIA

[75] Inventor: Gideon Strassmann, Washington, D.C.

[73] Assignee: Otsuka Pharmaceutical Co., Ltd., Tokyo, Japan

[21] Appl. No.: 607,693

[22] Filed: Nov. 1, 1990

[51] Int. Cl.$^5$ .................... A61K 37/22; A61K 45/05; A61K 37/24
[52] U.S. Cl. ................................. 424/450; 424/851; 514/2; 530/399
[58] Field of Search ................... 424/450, 85.1; 514/2; 530/399

[56] References Cited

U.S. PATENT DOCUMENTS

| | | | |
|---|---|---|---|
| 4,808,402 | 2/1989 | Leibovich et al. | 424/423 |
| 4,847,201 | 7/1989 | Kaswasaki et al. | 435/70 |
| 4,868,119 | 9/1989 | Clark et al. | 435/70 |
| 4,879,111 | 11/1989 | Chong | 424/85.2 |
| 4,879,227 | 11/1989 | Clark et al. | 435/70 |
| 4,916,118 | 4/1990 | Fidler et al. | 514/16 |
| 4,921,837 | 5/1990 | Donahue | 514/2 |

FOREIGN PATENT DOCUMENTS 0261592 3/1988 European Pat. Off. .
0328061 8/1989 European Pat. Off. .

OTHER PUBLICATIONS

Karbassi et al., J. Immunol. 139, 417–421 (1987).
Beutler et al., "The Common Mediator of Shock, Cachexia, and Tumor Necrosis", *Advances in Immunology*, vol. 42:213-231 (1988).
Brenner et al., "Tumor Necrosis Factor-α Inhibits Albumin Gene Expression in a Murine Model of Cachexia", *Journal of Clinical Investigation*, vol. 85:248-255 (Jan. 1990).
Fleit et al., "Interferon Induction in Marrow-Derived Macrophages: Regulation by L Cell Conditioned Medium", *Journal of Cellular Physiology*, vol. 108:347-352 (1981).
Sampson-Johannes et al., "Enhancement of Human Monocyte Tumoricidal Activity by Recombinant M-CSF", *Journal of Immunology*, vol. 141(10):3680-3686 (Nov. 15, 1988).
Karbassi et al., "Enhanced Killing of *Candida albicans* by Murine Macrophages Treated with Macrophage Colony-Stimulating Factor: Evidence for Augmented Expression of Mannose Receptors", *Journal of Immunology, vol. 139(2):417-421 (Jul. 15, 1987).*
Lawson et al., "Metabolic Approaches to Cancer Cachexia", *Ann. Rev. Nutr.,* vol. 2:277-301 (1982).
Lee et al., "CSF-1-Induced Resistance to Viral Infection in Murine Macrophages", Journal of Immunology, vol. 138:3019-3022 (1987).
Mahony et al., "Comparison of Weight Loss Induced by Recombinant Tumor Necrosis Factor with that Produced by a Cachexia-Inducing Tumor", Br. J. Cancer, vol. 57:385-389 (1988).
Michie et al., "Tumor Necrosis Factor and Endotoxin Induce Similar Metabolic Responses in Human Beings", *Surgery*, vol. 104(2):280-286 (Aug. 1988).
Mufson et al., "Macrophage Colony-Stimulating Factor Enhances Monocyte and Macrophage Antibody-Dependent Cell-Mediated Cytotoxicity", Cellular Immunology, vol. 119:182-192 (1989).
Ralph, "Activating Factors for Nonspecific and Antibody-Dependent Cytotoxicity by Human and Murine Mononuclear Phagocytes", Lymphokine Research, vol. 3(4):153-161 (1984).
Ralph et al., "Molecular Biological Properties of Human Macrophage Growth Factor, CSF-1", *Cold Spring Harbor Symposia on Quantitative Biology*, vol. LI:679-683 (1986).
Ralph et al., "Molecular Biology, Cell Biology and Clinical Future of Myeloid Growth Factors", *The Year in Immunology*, vol. 5:103-125 (1989).
Retzinger et al., "The Role of Surface in the Biological Activities of Trehalose 6,6'-Dimycolate", *J. Biol. Chem.*, vol. 256:8208-8216 (Aug. 10, 1981).
Sherry et al., "Cachectin/Tumor Necrosis Factor Exerts Endocrine, Paracrine, and Autocrine Control of Inflammatory Responses", Journal of Cell Biology, vol. 107:1269-1277 (Oct. 1988).
Sherry et al., "Anticachectin/Tumor Necrosis Factor-α Antibodies Attenuate Development of Cachexia in Tumor Models", *FASEB Journal*, vol. 3:1956-1962 (Jun. 1989).
Silva et al., "Mouse Cachexia Induced by Trehalose Dimycloate from *Nocardia Asteroides*", *Journal of General Microbiology*, vol. 134:1629-1633 (1988).
Silva et al., "Tumor Necrosis Factor (Cachectin) Mediates Induction of Cachexia by Cord Factor from Mycobacteria", *Infection and Immunity*, vol. 56(12):3067-3071 (Dec. 1988).
Suzu et al., "Enhancing Effect of Human Monocytic Colony-Stimulating Factor on Monocyte Tumoricidal Activity", *Cancer Research*, vol. 49:5913-5917 (Nov. 1, 1989).
Theologides, "Cancer Cachexia", *American Cancer Society*, vol. 43(5):2004-2012 (May 1979 Supp.).
Tisdale et al., "Inhibition of Weight Loss by ω-3 Fatty Acids in an Experimental Cachexia Model", *Cancer Research*, vol. 50:5022-5026 (Aug. 15, 1990).

(List continue on next page.)

Primary Examiner—Thurman K. Page
Assistant Examiner—G. S. Kishore
Attorney, Agent, or Firm—Finnegan, Henderson, Farabow, Garrett & Dunner

[57] ABSTRACT

A method for treating cachexia is provided, comprising the step of administering to a patient an amount of macrophage colony-stimulating factor (M-CSF) effective for said treatment.

6 Claims, No Drawings

OTHER PUBLICATIONS

Tracey et al., "Cachectin/TNF Mediates the Pathophysiological Effects of Bacterial Endotoxin/Lipopolysaccharide (LPS)", *Prog. Clin. Biol. Research*, vol. 242:77-88 (1988).

Tracey et al., "Cachectin/Tumor Necrosis Factor Induces Cachexia, Anemia, and Inflammation", *J. Exp. Med.*, vol. 167:1211-1227 (Mar. 1988).

Van Eys, "Nutrition and Cancer: Physiological Interrelationships", Ann. Rev. Nutr., vol. 5:435-461 (1985).

Vogel et al., "Recombinant Interleukin-1α and Recombinant Tumor Necrosis FActor α Synergize In Vivo to Induce Early Endotoxin Tolerance and Associated Hematopoietic Changes", *Infection and Immunity*, vol. 56(10):2650-2657 (Oct. 1988).

Warren et al., "Macrophage Growth Factor CSF-1 Stimulates Human Monocyte Production of Interferon, Tumor Necrosis Factor, and Colony Stimulating Activity", *Journal of Immunology*, vol. 137(7):2281-2285 (Oct. 1, 1988).

Wing et al., "Changes in Serum Colony-Stimulating Factor and Monocytic Progenitor Cells During *Listeria monocytogenes* Infection in Mice", Infection and Immunity, vol. 45(1):180-184 (Jul. 1984).

Hughes et al., "Modulation of Tumor Necrosis Factor Activities by a Potential Anticachexia Compound, Hydrazine Sulfate", *Int. J. Immunopharmacol.*, vol. 11(5):501-507 (1989) (abstract only).

Aukerman et al., "Preclinical Pharmacology of Recombinant Human M-CSF", *J. Leukocyte Biology*, p. 102, No. 292 (Supplement 1990) (abstract).

Lathey et al., "Weight Loss in Obese Mice Persistently Infected with Lymphocytic Choriomeningitis Virus is Not Associated with Elevated Tumor Necrosis Factor/Cachectic Activity in Peritoneal Macrophages", *Am. J. Pathol.*, 132(3):586-592 (Sep. 1988).

Sabatini et al., "Stimulation of Tumor Necrosis Factor Release from Monocytic Cells by the A375 Human Melanoma via Granulocyte-Macrophage Colony-Stimulating Factor", *Cancer Res.*, vol. 50(9):2673-2678 (May 1, 1990) (abstract only).

METHOD FOR THE TREATMENT OF BACTERIAL CAUSED WEIGHT LOSS AND/OR HYPOGLYCEMIA

FIELD OF THE INVENTION

The present invention relates to a method for treating cachexia in a patient, particularly a human being, by the administration of macrophage colony-stimulating factor, hereinafter "M-CSF."

BACKGROUND OF THE INVENTION

Cachexia, a potentially lethal syndrome afflicting mammals, frequently complicates the treatment of infection, inflammation and cancer. It is characterized by profound weight loss caused by wasting of body fat (adipose) and muscle (protein). Tracey et al., *J. Exp. Med.*, Vol. 167, 1,211–1,227 (March 1988). Lawson et al., *Ann. Rev. Nutr.*, 2:277–301 (1982). Anorexia, anemia, and weakness may also occur in cachexia. Tracey et al., supra. Cachexia may further be characterized by, inter alia, depression of glucose level (hypoglycemia) and elevation of triglyceride level (hypertriglyceridemia).

Cachexia may result from diverse causes such as age, cancer, and infections by parasites and by microorganisms such as bacteria, fungi, viruses and protozoa. Both acute and chronic infections or illnesses frequently cause cachexia. In fact, most chronic, fatal, nonneoplastic diseases terminate in cachexia (e.g. chronic disseminated infections, or prolonged insufficiency of heart, lungs, liver, kidneys, or the small intestines). Lawson et al., *Ann. Rev. Nutr.*, 2:277–301 (1982). Moreover, the syndrome is not alleviated by adequate caloric uptake. Indeed, weight loss may continue in cachexia even while an adequate diet is consumed. Silva et al., *J. General Microbiology*, Vol. 134, 1,629–1,633 (1988).

Researchers have studied cachexia induced by microbial infections, and by parasitic infections such as trypanosomiasis and leishmaniasis. Sherry et al., *J. Cell Biology*, Vol. 107, 1,269–1,277 (October 1988). The study of cachexia induced by microbial infections has shown that the syndrome may result from either the direct effect of the microorganism or from a toxin produced by the microorganism. For example, weight loss has been observed as a toxic manifestation in mice upon injection with endotoxin, the lipopolysaccharide (LPS) derived from gram-negative bacteria. Vogel et al., *Infection and Immunity*, Vol. 56, No. 10, 2,650–2,657 (October 1988).

Indeed, the toxin produced by a microorganism has been used to create a model for the study of cachexia. In this regard, cachexia has been induced by intraperitoneal injection into mice of trehalose dimycolate (TDM), isolated from Nocardia asteroides. Silva et al., *J. General Microbiology*, Vol. 134, 1,629–1,633 (1988). Researchers have studied the mechanism by which TDM, also known as cord factor (CF), a toxic glycolipid from mycobacteria, induces cachexia. Silva et al., *Infection and Immunity*, Vol. 56, No. 12, 3,067–3,071 (December 1988). That laboratory observed that administration of CF markedly reduced body weight; the animals became severely wasted and exhibited hypertriglyceridemia, hypoglycemia, and high levels of tumor necrosis factor in plasma. Dexamethasone was found to partially inhibit the cachexia-inducing action of CF.

Recent research has focused on the physiology related to cachexia. For example, the increase in circulating triglycerides observed has been attributed to systemic suppression of lipoprotein lipase (LPL). Tracey et al., *J. Exp. Med.*, Vol 167, 1,211–1,227 (March 1988). It has been reported, however, that transplantable adenocarcenoma of the colon (MAC16) produces cachexia symptoms with concomitant hypotriglyceridemia. Mahony et al., *Br. J. Cancer*, 57, 385–389 (1988).

It has also been suggested that tumor necrosis factor, hereinafter "TNF", also known as "cachectin", Beutler et al., *Advances in Immunology*, Vol. 42, 213–231 (1988), may play a central role in cachexia. Tracey et al., *J. Exp. Med.*, Vol. 167, 1,211–1,227 (March 1988). Michie et al., *Surgery*, Vol. 104, No. 2, 286 (August 1988), reports that TNF may represent the primary stimulus that initiates many of the metabolic responses associated with sepsis and endotoxemia.

The role of TNF, however, is not clear. Although cachexia in cancer patients has been associated with the presence of TNF, this factor has not been uniformly detectable in the serum of cachectic patients with cancer. Sherry et al., *The FASEB J.*, Vol. 3, 1,956–1,962 (June, 1989). In one study, using both cachexia-inducing (MAC16) and non-cachexia-inducing (MAC13) adenocarcinomas, researchers concluded that weight loss produced by TNF arises from an anorexic effect that differs from the complex metabolic changes associated with cancer cachexia. Mahony et al., *Br. J. Cancer*, 57, 385–389 (1988). Similarly, in a study on viral-related cachexia, using mice infected persistently with lymphocytic choriomeningitis virus (LCMV), the laboratory concluded that the greater than 20% cachexia-like weight loss observed was apparently not associated with a measurable increase in TNF. Lathey et al., *Am. J. Pathol.*, 132(3):586–92 (September 1988).

The severe weight loss and debilative wasting of lean body mass of cachexia frequently complicates the treatment of patients suffering from malignancy or chronic infection. Indeed, cachexia contributes to cancer mortality. Some data indicate that as many as 30% of cancer patients die from cachexia, rather than tumor burden. Tracey et al., supra. One medical textbook notes that:

> "[t]he most common way in which malignancy leads to death is cachexia: the development of progressive weakness, weight loss, and wasting. Usually, there is a close correlation between the amount of malignant disease present and the severity of cachexia . . . In this weakened state, cancer patients are particularly susceptible to terminal infections, such as pneumonia, which often precipitates death." van Eys, *Ann. Rev. Nutr.*, 5:435–61 (1985) (based on "the second edition of Robbins' Textbook of Pathology).

The severity of cachexia may be unrelated to tumor size or parasite load, and profound wasting has been observed in patients with tumor burdens of only 0.01 to 5.0% body mass. If not reversed, physiological changes associated with cachexia lead to immunological deficiencies, organ failure, and multiple metabolic abnormalities. Tracey et al., *J. Exp. Med.*, Vol. 167, 1,211–1,227 (March 1988). Theologides, *Cancer*, May Supplement, Vol. 43, 2,004–2,012 (1979).

The physiological changes due to cachexia decrease the patient's tolerance to chemotherapy and radiation therapy, as well as increase the frequency of post-surgical complications. The nausea, vomiting, and anorexia induced by chemotherapeutic agents as well as radiation injury can be very severe. In addition, chemotherapy is a major factor in malnutrition. It is well recognized that therapy is often as debilitating as the cancer itself. The malnourished patient has a much narrower safe therapeutic margin for most oncologic therapy. van Eys, supra.

Further, median survival has been found to be significantly shorter in patients who had lost weight with most types of tumor examined. Lawson et al., *Ann. Rev. Nutr.*, 2:277-301 (1982).

The precise mechanisms by which the cachexia syndrome may cause death in some patients and perhaps contribute to it in others are not completely understood. Lawson et al., *Ann. Rev. Nutr.*, 2:277-301 (1982). Thus, the art has continued to search for effective methods for treating cachexia resulting from etiologies such as cancer or infectious diseases.

SUMMARY OF THE INVENTION

The instant invention provides a method for treating cachexia, comprising the step of administering to a patient an amount of macrophage colony-stimulating factor (M-CSF) effective for said treatment.

The invention contemplates treating all forms of cachexia, whether induced by infection, cancer, age or otherwise.

Additional objects and advantages of the invention will be set forth in part in the description which follows. It is to be understood that the general description above and the following detailed description are exemplary and explanatory only and do not limit the invention, as claimed.

DESCRIPTION OF THE PREFERRED EMBODIMENTS

The instant invention provides a method for treating cachexia resulting from infection, cancer, age or otherwise.

The claimed method can also be used to treat any of the symptoms associated with the cachexia syndrome. Thus, the method of the instant invention may be employed to mitigate or completely eliminate weight loss associated with wasting of body fat and muscle, hypertriglyceridemia, hypoglycemia, and anorexia. In addition, the claimed invention may be used to prevent loss of tissue in vital organs. The instant method is particularly useful in treating cachexia due to cancer or chronic infections.

The method of the instant invention may be used, for example, to treat cachexia arising as a result of infection, chronic or otherwise, caused by a unicellular or multicellular parasite, or microbe such as a bacteria, fungus, protozoa or virus, or a combination of these organisms. For example, the invention contemplates treatment of cachexia due to infections by the following organisms: infections due to gram-negative or gram-positive bacteria such as infections due to gram-positive cocci (pneumococcal, staphylococcal and streptococcal infections), infections due to gram-negative cocci (meningoccal infections), infections due to enteric gram-negative bacilli (coliform bacterial infections, typhoid fever, Salmonella infections, Shigella infections, cholera), mycobacterium, infections due to bacteria of the Hemophilus group (pertussis, influenza bacillus infections), tuberculosis infections, fungal infections (Candida), spirochetal and rickettsial infections, viral infections (influenza, hepatitis, Sendai, herpes) and infections due to protozoa (malaria, leishmaniasis).

The method of the instant invention is also useful in treating cachexia resulting from cancer. Treatment of cachexia resulting from either a TNF- or non-TNF-producing cancer is within the scope of the instant invention. Thus, for example, all forms of cachexia produced by carcinomas or leukemias are treatable by the instant method. Treatment according to the claimed invention will mitigate or totally eliminate the symptoms of cachexia, such as wasting and other physiological changes. This treatment may allow the patient to better tolerate chemotherapy or radiation therapy, improving the patient's overall prognosis and quality of life.

As used herein, the term "M-CSF" of the invention relates to a particular type of colony-stimulating factor. Colony-stimulating factors are glycoproteins that regulate the production of hematopoietic cells. At least four distinct colony-stimulating factors control proliferation and differentiation of granulocytes and/or macrophages from hematopoietic precursors.

Macrophage colony-stimulating factor (M-CSF, also known as CSF-1) can selectively stimulate the survival, proliferation, and differentiation of mononuclear phagocyte lineage cells. Studies have also shown that M-CSF also stimulates effector functions of mature monocytes such as antifungal activity and lymphokine-induced tumoricidal activity. Stanley, E.R. and Gulbert, L.T., "Method for the Purification, Assay, Characterization and Target Cell Binding of Colony-Stimulating Factor [CSF-1]", J. Immunologic Methods 42: 253-284 (1981); Karbassi, A., et al., "Enhanced Killing of Candida Albicans by Murine Macrophages Treated with Macrophage Colony-Stimulating Factor: Evidence for Augmented Expression of Mannose Receptors", J. Immunology 139: 417-421 (1987); Metcalf, D. "The Molecular Biology and Functions of the Granulocyte macrophage Colony-Stimulating Factors," Blood 67:257 (1986); and Ralph P. and Nakoinz, I., "Stimulation of Macrophage Tumoricidal Activity by Growth and Differentiation Factor CSF-1", Cellular Immunology 105: 270-279 (1987).

The method of the instant invention comprises the use of any and all forms of M-CSF, including whole intact M-CSF as well as M-CSF that has been truncated or otherwise altered by standard biochemical or recombinant techniques. See, U.S. application Ser. No. 07/304,692, filed Feb. 1, 1989, entitled "Human Colony-Stimulating Factors," to Takahashi, M. et. al., incorporated herein by reference. Any form of M-CSF that provides the desired mitigation or total elimination of cachexia is contemplated within the invention. M-CSF thus refers both to naturally occurring M-CSF or recombinant M-CSF, including derivatives thereof, for example, as described in European Patent Publications No. 261592 and No. 328061; and U.S. Pat. No. 4,868,119. The M-CSF may be of human or other mammalian origin, but is preferably of human origin.

With respect to administration to a patient according to the method of the instant invention, M-CSF may be given as is or formulated into pharmaceutical compositions comprising an effective amount of M-CSF and one or more pharmacologically acceptable nontoxic carriers, diluents or adjuvants. Such compositions are, for example, in the form of liquid preparations including solution, suspension, and emulsion preparations. Such compositions may also be solid preparations given as is or reconstituted to a liquid for use by addition of a suitable carrier.

Pharmaceutical carriers may be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions may also be employed as liquid carriers, particularly for injectable solutions. Suitable pharmaceutical excipients include starch, glucose, lactose, sucrose, gelatin, malt, rice, flour, chalk, silica gel, magnesium carbonate, magnesium stearate, sodium stearate, glycerol monostearate, talc, sodium chloride, dried skim milk, glycerol, propylene glycol, water, ethanol and the like. These compositions can take the form of solutions, suspensions, tablets, pills, capsules, powders, sustained-release formulations and the like. Suitable pharmaceutical carriers are described in "Remington's Pharmaceutical Sciences" by E.W. Martin. M-CSF may be administered in aggregate form with liposomes, for example, in accordance with the liposome-associated M-CSF compositions disclosed in copending U.S. application Ser. No. 07/505,584, to Gideon Strassmann, filed Apr. 6, 1990, incorporated herein by reference.

M-CSF may be administered in the appropriate form according to methods known to those skilled in the art, such as orally, intravenously, subcutaneously, intracutaneously or intramuscularly. Intraperitoneal as well as subcutaneous injection are preferred methods of administration.

It is particularly preferred to administer M-CSF according to the method of the invention before, as well as after, the onset of cachexia or exposure to the factor giving rise to cachexia.

Persons of ordinary skill in the art will be able to determine the dosage of M-CSF effective to achieve the object of the invention. Dosages selected are those which mitigate or completely eliminate the symptoms associated with cachexia. Determination of the appropriate dosages for treatment are routinely made by those of ordinary skill in the art and are within the array of tasks routinely performed by them without undue experimentation. While the amount of M-CSF to be given in any form is not limited specifically, and can be determined suitably according to the age and sex of the patient, the degree of disease, etc., M-CSF may be administered, for example, at a dose of about 0.0001 to about 1 mg/kg/day based on the amount of M-CSF in terms of protein amount. The dose may be given daily, either singly or dividedly.

The term "patient" is used herein in its broadest sense to mean mammals, including humans, as well as other mammals such as laboratory animals, for example, dogs, cats, guinea pigs, mice, and rats.

The invention is further illustrated by the following examples, which are intended solely to exemplify and not to limit the invention.

EXAMPLES

A. The Preparation of Macrophage Colony-Stimulating Factor

The following illustrates a method for the preparation of M-CSF. The M-CSF may be obtained by the renaturation and purification of human truncated M-CSF expressed in E. coli.

(1) Construction and Expression

The expression of a truncated form of human M-CSF was performed using two cistronic expression systems. The COS expression plasmid designated pcDhMCSF11-185, which encodes N-terminal 185 amino acid residues of the 554 amino acid M-CSF precursor was digested with Scal and BamHi restriction enzymes. The resultant fragment (about 450 bp) was ligated with a synthetic linker which possessed an internal SD sequence, a termination codon for the first cistron and an initiation codon for the second cistron. The ligated fragment was inserted between the Xbal and BamHi sites of prepIL-2D8. The resultant plasmid, ptrpI1-2X M-CSF101, coding for a 151 amino acid sequence of M-CSF was then transformed into E. coli by the CaCl2 method. Such recombinant techniques are provided in the copending U.S. application Ser. No. 07/304,692, filed Feb. 1, 1989, entitled "Human Colony-Stimulating Fators," to Takahashi, M. et. al.

(2) Renaturation

The transformed E. coli cells were shaken in supplemented M9 medium which also contained ampicillin. The cells were harvested and pelleted and washed with Triton X-100. The final pellet contained an inclusion body containing the truncated M-CSF. The pellet was solubilized in 7.0M guanidin hydrochrolide and 25 mM 2-mercaptoethanol with stirring for 4 hours at room temperature. The solubilized pellet was slowly dropped into 2,000 ml of glutathione solution (0.5 mM reduced, 0.1 mM oxidized glutathione and 2.0M urea in 50 mM Tris/HCL, ph 8,5) with intense stirring. The solution was kept at 4° C. for 48 hours.

After 10 ml of the renatured solution was concentrated to 500 ul in an Amicon membrane, the solution was applied at a rate of 0.7 ml/min to a gel filtration HPLC on Shodex WS-803 column previously equilibrated with 40 mM sodium phosphate containing 0.3M NaCl, ph 6.8. The fractions were collected and assayed for M-CSF activity.

(3) Purification

The renatured solution was centrifuged and the supernatant applied to QAE-ZeTA Prep Cartridge 100 from Pharmacia-LKB which was previously equilibrated with 50 mM Tris/HCl at ph 8.5 and eluted with 0.5M NaCl in 50 mM Tris/HCl, pH 8.5.

After ammonium sulfate precipitation, the supernatant was applied to a TSK-gel Phenyl-5PW HPLC column (Toso, 21.5×1,500 mm), preequilibrated with 40 mM sodium phosphate, pH 7.4 and containing a saturated ammonium sulfate solution. The active fragments were obtained at 6-3% ammonium sulfate and concentrated and exchanged against 40 mM sodium phosphate, pH 7.4.

The concentrated sample was applied to a TSK-gel DEAE 5PW column (Toso, 21.5×150 mm) preequilabrated with 40 mM sodium phosphate, pH 7.4, and eluted at a flow rate of 3 ml/min by a NaCl gradient.

B. Experimental Procedures

The following procedures were employed in Experiments 1 through 4 below.

(i) Mice:

C57BL/6 pathogen-free female mice with an average weight of 18-20 gm were used.

(ii) Endotoxin-Induced Cachexia:

Lipopolysaccharide (LPS), obtained from Sigma (Cat. #L-2880), *Escherichia coli* serotype 055:B5, was used. Ten micrograms of LPS were diluted in phosphate buffered saline, hereinafter "PBS", (pH 7.4) and injected intraperitoneally, hereinafter "IP". (See Vogel et al., *Infection and Immunity*, Vol. 56, No. 10, 2,650–2,657 (October 1988)).

(iii) Trehalose 6,6-Dibehenate (TDB)-Induced Cachexia:

TDB (Sigma Cat #T-2268) is a synthetic analog of mycobacteria-derived trehalose dimycolate (cord factor—the active component of complete Freund's adjuvent) (See Retzinger et al., *J. Biol. Chem.*, Vol. 256, 8,208–8,216 (Aug. 10, 1981).) TDB was dissolved in chloroform:methanol (9:1), and then dried under a nitrogen stream and solubilized in light mineral oil. The mixture was then vortexed and sonicated for 10 minutes in a bath sonicator (Laboratory Supplies Co., Hicksville, N.Y., 300 watts). Immediately after sonication 15 μg of TDB in 0.1 ml mineral oil was injected IP (Silva et al., *J. General Microbiology*, 134, 1,629–1,633 (1988)). Mice were weighed initially and at 24 hr. intervals from injection.

(iv) Glucose Determination

Blood was drawn from the retrobital plexus and serum was obtained by centrifugation. Ten microliters of serum was analyzed for glucose levels by an Ektachem DT-60 automatic analyzer (Eastman Kodak).

Experiment 1. Effect of M-CSF on TDB-Induced Cachexia

| Group | I. Protocol | |
|---|---|---|
| | Treatment Time (days) | |
| | −1 | 0 |
| 1 | PBS | M.O./PBS |
| 2 | PBS | TDB/PBS |
| 3 | M-CSF | TDB/M-CSF |

On day −1 C57BL/6 female mice were injected with 0.1 ml PBS (Groups 1 and 2) or M-CSF (50 μg) intraperitoneally (Group 3). On day 0 Group 1 received 0.1 ml of mineral oil (M.O. IP), while Groups 2 and 3 received M.O. containing 15 μg of trehalose dibehenate (TDB). Four hours later, Groups 1 and 2 received an IP injection of PBS, while Group 3 received 50 μg of M-CSF. On day 2, glucose levels were determined.

Thus, Group 1 was a control group, to which nonactive materials (PBS and mineral oil) were administered to assess the effect of injections alone. Group 2 was a group receiving the cachexia-inducing agent TDB, to assess the effects of TDB-induced cachexia. Group 3 was a group treated with both the cachexia-inducing agent TDB, and with M-CSF according to the method of the invention, to assess the effectiveness of M-CSF in mitigating the effects of TDB-induced cachexia.

Experiment 1. Effect of M-CSF on TDB-Induced Cachexia

| | | IIA. Results: Weight Loss | | |
|---|---|---|---|---|
| | No. of mice | Mean Weight +/− S.D. Time (days) | | |
| Group | per Group | 0 | 1 | 2 |
| 1 | 6 | 18.88 +/− 1.36 | 19.46 +/− 1.39 (0.58)+ | 19.16 +/− 1.78 |
| 2 | 8 | 19.26 +/− 1.09 | 18.05 +/− 0.69 (−1.21)* | 17.58 +/− 0.67 |
| 3 | 8 | 18.97 +/− 0.17 | 18.50 +/− 0.46 (−0.47)+ | 18.18 +/− 0.66 |

*Statistical difference between the mean weight of Group 2 on day 1 to that on day 0 is p = 0.02 by student's T test.
+No statistical difference from the mean weight of the same group on the prior day.
Figures in parenthesis represent the change of mean weight between day 1 and day 0.

The above data illustrate that administration of TDB to one group of animals (Group 2) induced a statistically significant drop in the mean weight, where no such drop was observed in the control group (Group 1). The data also illustrate that administration of M-CSF according to the instant invention to TDB-treated animals (Group 3) mitigated the TDB-induced weight loss.

| | IIB. Results: Glucose Level |
|---|---|
| Group | Glucose mg/DL ± S.D. |
| 1 | 200 ± 14 |
| 2 | 167 ± 28* |
| 3 | 203 ± 18 |

*Statistical difference of Group 1 vs. 2 or Group 2 vs. 3: p = 0.02. No difference between Groups 1 and 3.

The above data also illustrate that hypoglycemia was induced in TDB-treated animals (Group 2), but that administration of M-CSF according to the instant invention to TDB-treated animals (Group 3) resulted in glucose levels not significantly different from the control group (Group 1).

This experiment demonstrates that the M-CSF administration of the instant invention alleviates weight loss and hypoglycemia resulting from cachexia induced by TDB.

Experiment 2. Effect of M-CSF on TDB-Induced Cachexia

| | I. Protocol | | | | |
|---|---|---|---|---|---|
| | Treatment Time (days) | | | | |
| Group | −1 | 0 | 1 | 2 | 3 |
| 1 | PBS | M.O./PBS | PBS × 2 | PBS × 2 | Sacrifice |
| 2 | PBS | TDB/PBS | PBS × 2 | PBS × 2 | Sacrifice |
| 3 | M-CSF | TDB/M-CSF | M-CSF × 2 | M-CSF × 2 | Sacrifice |
| 4 | M-CSF | TDB/M-CSF | M-CSF × 2 | M-CSF × 2 | Sacrifice |

On day −1, eight C57BL/6 female mice per group were injected with PBS (0.1 ml) intraperitoneally (Groups 1 and 2), or rh M-CSF (10 μg) intraperitoneally (IP) (Group 3) or subcutaneously (SC) (Group 4). On day 0 mice were injected with mineral oil (M.O., 0.1 ml) (Group 1) or M.O. containing 15 μg of trehalose dibehenate (TDB) (Groups 2, 3 and 4), followed by a second injection four hours later of PBS (Groups 1 and 2) or M-CSF (Groups 3 and 4). On days 1 and 2, M-CSF (10 μg) (Groups 3 and 4) or PBS (Groups 1 and 2) were injected twice daily at 9 am and 5 pm. Weight was determined daily at 9 am. On day 3 the mice were sacrificed.

Thus, Group 1 was a control group, to which nonactive materials (PBS and mineral oil) were administered to assess the effect of injections alone. Group 2 was a group receiving the cachexia-inducing agent TDB, to assess the effects of TDB-induced cachexia. Groups 3 and 4 were groups treated with both the cachexia-inducing agent TDB, and with M-CSF according to the method of the invention, to assess the effectiveness of M-CSF in mitigating the effects of TDB-induced cachexia. Groups 3 and 4 received M-CSF via intraperitoneal and subcutaneous injections, respectively, to assess the relative effectiveness of these modes of administration.

Experiment 2. Effect of M-CSF on TDB-Induced Cachexia

| | II. Results | | |
|---|---|---|---|
| | Percent change of weight (from day 0) Time (days) | | |
| Group | 1 | 2 | 3 |
| 1 | +1.7 | +5.1 | +6.0 |
| 2 | −6.5 | −5.3 | −3.0 |
| 3 | −3.2 | −0.1 | +0.04 |
| 4 | −2.4 | +1.2 | +1.5 |

The mean weight of Group 2 on day 2 was found to be statistically different ($p = 0.01$ by student's T test) from that on day 0. There was no statistical difference between the mean weight of either Groups 3 or 4 on day 2 to the mean weight of either group on day 0.
% change of weight was calculated by the formula:
$$\frac{\text{Mean weight day x} - \text{Mean weight day 0}}{\text{Mean weight day 0}} \times 100$$

The above data illustrate that a drop in mean weight (calculated through the use of individual animal weights) was induced in animals treated with TDB (Group 2). The above data also illustrate that administration of M-CSF according to the instant invention, both by intraperitoneal (Group 3) and subcutaneous (Group 4) injection, alleviated TDB-induced weight loss.

This experiment demonstrates that M-CSF administration according to the instant invention alleviates weight loss resulting from cachexia induced by TDb.

Experiment 3. Effect of M-CSF on LPS-Induced Cachexia

| | I. Protocol | |
|---|---|---|
| | Treatment | |
| Group | LPS | Treatment |
| 1 | PBS | PBS |
| 2 | 10 μg IP | PBS |
| 3 | 10 μg IP | M-CSF 10 μg IP |
| 4 | 10 μg IP | M-CSF 10 μg SC |

Eight C57BL/6 female mice per group were injected (a) on day −1 with PBS (Groups 1 and 2) or M-CSF (Groups 3 and 4); (b) on day 0 with LPS (Groups 2, 3 and 4) or PBS (Group 1); and (c) on day 0, 4 hours after receiving the injections in (b), with PBS (Groups 1 and 2) or M-CSF (Groups 3 and 4). Twenty-four hours after LPS injection mice were weighed and bled.

Thus, Group 1 was a control group, to which nonactive material was administered to assess the effect of injections alone. Group 2 was a group receiving the cachexia-inducing agent LPS, to assess the effects of LPS-induced cachexia. Groups 3 and 4 were groups treated with both the cachexia-inducing agent LPS, and with M-CSF according to the method of the invention, to assess the effectiveness of M-CSF in mitigating the effects of LPS-induced cachexia. Groups 3 and 4 received M-CSF via intraperitoneal (IP) and subcutaneous (SC) injections, respectively to assess the relative effectiveness of these modes of administration.

The following results represent the mean change between day 1 and day 0 of individual animals.

Experiment 3. Effect of M-CSF on LPS-Induced Cachexia

| | II. Results | | |
|---|---|---|---|
| Group | Δ Change (gm) ± S.D. | Δ Change from initial body weight % ± S.D. | Glucose mg/DL ± S.D. |
| 1 | +0.13 ± 0.16 | +0.05 ± | 203 ± 20 |
| 2 | −2.51 ± 0.64 | −12.97 ± 3.3 | 144 ± 7 |
| 3 | −1.35 ± 0.68* | −7.01 ± 3.4* | 166 ± 15* |
| 4 | −1.96 ± 0.17+ | −10.44 ± 1.8+ | 139 ± 5+ |

*Statistical difference between Groups 3 and 2 is $p = 0.012$ (Student's T Test)
+No statistical difference between Groups 4 and 2.

The above data illustrate that a drop in the mean weight of the tested animals was induced by LPS (Group 2). The above data also illustrate that intraperitoneal administration of M-CSF according to the instant invention in LPS-treated animals (Group 3) alleviated weight loss and hypoglycemia.

This experiment demonstrates that intraperitoneal injection of M-CSF according to the instant invention partially alleviates weight loss and hypoglycemia resulting from cachexia induced by LPS.

Experiment 4: Effect of M-CSF on Internal Organs

I. Protocol

As indicated in the following chart, six C57BL/6 female mice per group were injected with PBS or with 10 μg of M-CSF on day −1 and 4 hrs after LPS injection (10 μg/mouse on day 0). All injections were IP. On day +1, mice were killed and weight determined.

Thus, Group 1 was a group receiving the cachexia-inducing agent LPS, to assess the effects of LPS-induced cachexia. Group 2 was treated with both the cachexia-inducing agent LPS, and with M-CSF according to the method of the invention, to assess the effectiveness of M-CSF in mitigating the effects of LPS-induced cachexia.

| | | II. Results | | | | |
|---|---|---|---|---|---|---|
| | Treatment | % Change From Initial Body | Organ Weight ± S.D. (mg) | | | |
| Group | day −1, day 0, + 4 hrs. | Weight ± S.D. | Heart | Kidney | Liver | Spleen |
| 1 | PBS, LPS, PBS | −10.47 ± 3.42 | 86 ± 3 | 105 ± 5 | 814 ± 77 | 60 ± 7 |

| Group | Treatment day −1, day 0, + 4 hrs. | % Change From Initial Body Weight ± S.D. | Organ Weight ± S.D. (mg) | | | |
|---|---|---|---|---|---|---|
| | | | Heart | Kidney | Liver | Spleen |
| 2 | M-CSF$_{10}$, LPS, M-CSF$_{10}$ | −6.95 ± 1.17* | 102 ± 7+ | 106 ± 6 | 872 ± 24 | 76 ± 9++ |

Statistics (Student's T Test)
*Group 1 vs. 2 p = 0.03
+Group 2 (Heart) vs. 1, p = 0.0008 (The mean weight of hearts of age matched control mice (N = 6) is 102 ± 2 mg)
  Group 2 (Kidney or Liver) vs. 1, No Difference
++Group 2 (Spleen) vs. 1, p = 0.02

The above data illustrate that administration of M-CSF according to the instant invention to LPS-treated animals (Group 2) alleviated overall body weight loss as compared with LPS-treated animals receiving no M-CSF. The above data also illustrate that M-CSF administration alleviated tissue loss in the heart and spleen of LPS-treated animals (Group 2) as compared with LPS-treated animals receiving no M-CSF (Group 1).

This experiment demonstrates that M-CSF administration according to the instant invention alleviates the drop in overall body weight, as well as the drop in weight of the heart and spleen tissues, resulting from LPS-induced cachexia.

Other embodiments of the invention will be apparent to those skilled in the art from a consideration of the specification and practice of the invention disclosed herein. It is intended that the specification and examples be considered as exemplary only, with the true scope and spirit of the invention being indicated by the following claims.

What is claimed is:

1. A method of treating bacterial caused weight loss and/or hypoglycemia, comprising the step of administering to a patient an amount of macrophage colony-stimulating factor (M-CSF) effective for said treatment.

2. The method of claim 1, wherein said weight loss and/or hypoglycemia is the result of infection by a gram-positive bacterium.

3. The method of claim 1, wherein said weight loss and/or hypoglycemia is the result of infection by a gram-negative bacterium.

4. The method of claim 1, wherein said M-CSF is whole, intact M-CSF.

5. The method of claim 1, wherein said M-CSF is truncated M-CSF.

6. The method of claim 1, wherein said M-CSF is administered in the form of an aggregate with liposomes.

* * * * *